(12) United States Patent
Bennett et al.

(10) Patent No.: US 7,545,969 B2
(45) Date of Patent: Jun. 9, 2009

(54) METHOD AND SYSTEM FOR WIDE-AREA ULTRAVIOLET DETECTION OF FORENSIC EVIDENCE

(75) Inventors: Mischell A. Bennett, Madison, AL (US); Odell Huddleston, Jr., Huntsville, AL (US)

(73) Assignee: Alliant Techsystems Inc., Minneapolis, MN (US)

( * ) Notice: Subject to any disclaimer, the term of this patent is extended or adjusted under 35 U.S.C. 154(b) by 794 days.

(21) Appl. No.: 11/014,524

(22) Filed: Dec. 16, 2004

(65) Prior Publication Data
US 2006/0133643 A1 Jun. 22, 2006

(51) Int. Cl.
*G06K 9/00* (2006.01)

(52) U.S. Cl. .................. 382/141; 250/365; 250/372; 250/461.1; 356/51; 382/133; 382/218; 382/284

(58) Field of Classification Search .............. 250/365, 250/372, 458.1, 461.1; 356/51, 317, 318; 382/100, 133, 144, 218, 219, 278, 284, 141
See application file for complete search history.

(56) References Cited

U.S. PATENT DOCUMENTS

| | | | |
|---|---|---|---|
| 4,897,551 A | 1/1990 | Gersh et al. | |
| 4,933,816 A | 6/1990 | Hug et al. | |
| 4,983,846 A | 1/1991 | Rios et al. | |
| 5,034,615 A | 7/1991 | Rios et al. | |
| 5,422,719 A | 6/1995 | Goldstein | |
| 5,455,674 A | 10/1995 | Purcell | |
| 5,485,530 A | 1/1996 | Lakowicz et al. | |
| 5,804,384 A * | 9/1998 | Muller et al. ................ | 435/6 |
| 6,009,340 A | 12/1999 | Hsia | |
| RE37,136 E | 4/2001 | Vezard | |
| 6,306,662 B1 | 10/2001 | Menzel | |
| 6,313,467 B1 | 11/2001 | Shafer et al. | |
| 6,392,238 B1 | 5/2002 | Vezard | |
| 6,485,981 B1 * | 11/2002 | Fernandez ................ | 436/71 |
| 6,633,043 B2 * | 10/2003 | Hegazi et al. ............ | 250/461.1 |
| 6,633,662 B2 * | 10/2003 | Ravkin ................ | 382/133 |
| 6,636,701 B1 | 10/2003 | Vezard | |
| 6,648,506 B2 * | 11/2003 | McGrath et al. ............ | 374/161 |

(Continued)

FOREIGN PATENT DOCUMENTS

WO     WO 95/28632     10/1995

OTHER PUBLICATIONS

European Search Report dated Feb. 27, 2006.

*Primary Examiner*—Gregory M Desire
(74) *Attorney, Agent, or Firm*—TraskBritt (57) ABSTRACT

The present invention comprises a method for detecting and analyzing forensic evidence. A digital image is taken of background radiation from a suspected-evidence area suspected to contain evidence. The suspected-evidence area is exposed to a high-intensity pulse of ultraviolet radiation. Another digital image is taken of fluorescence within the exposed suspected-evidence area. The digital images are processed to create a composite digital image showing regions of evidence. The composite digital image is analyzed to determine the wavelength of fluorescent radiation emitted by the regions of evidence. Composite evidence image and the analysis results are displayed. The present invention also comprises a forensic evidence detection and analysis system that includes a digital camera, an ultraviolet light source, a computer and display, and a computer program installed on the computer.

31 Claims, 4 Drawing Sheets

U.S. PATENT DOCUMENTS

| | | | |
|---|---|---|---|
| 6,665,427 B1 | 12/2003 | Keagy et al. | |
| 6,678,398 B2 | 1/2004 | Wolters et al. | |
| 6,914,250 B2* | 7/2005 | Seville | 250/458.1 |
| 7,154,661 B2* | 12/2006 | Seah et al. | 359/326 |
| 7,224,826 B2* | 5/2007 | Shibazaki et al. | 382/128 |
| 7,262,419 B2* | 8/2007 | Richardson | 250/458.1 |
| 7,289,205 B2* | 10/2007 | Yaroslavsky et al. | 356/317 |
| 7,330,749 B1* | 2/2008 | Bhunachet | 600/476 |
| 2002/0107668 A1* | 8/2002 | Costa et al. | 702/189 |
| 2003/0005303 A1* | 1/2003 | Auslander et al. | 713/176 |
| 2003/0173525 A1* | 9/2003 | Seville | 250/458.1 |
| 2004/0001196 A1* | 1/2004 | Shibazaki et al. | 356/129 |
| 2004/0021086 A1 | 2/2004 | Verrier et al. | |
| 2004/0046874 A1 | 3/2004 | Tse | |
| 2004/0099809 A1 | 5/2004 | Verrier et al. | |
| 2004/0119975 A1 | 6/2004 | Ostler et al. | |
| 2004/0120151 A1 | 6/2004 | Ostler et al. | |
| 2004/0169854 A1 | 9/2004 | Vo-Dinh et al. | |
| 2004/0186351 A1* | 9/2004 | Imaizumi et al. | 600/160 |
| 2004/0197771 A1 | 10/2004 | Powers et al. | |
| 2004/0247161 A1 | 12/2004 | Storm | |
| 2005/0013463 A1* | 1/2005 | Reed et al. | 382/100 |
| 2005/0259256 A1* | 11/2005 | Anselmetti et al. | 356/344 |
| 2006/0126061 A1* | 6/2006 | Kreckel et al. | 356/241.1 |

* cited by examiner

METHOD AND SYSTEM FOR WIDE-AREA ULTRAVIOLET DETECTION OF FORENSIC EVIDENCE

FIELD OF THE INVENTION

The present invention relates to a method for detecting and analyzing forensic evidence from an examined surface.

BACKGROUND OF THE INVENTION

In the field of forensic science, criminal investigators are seeking improved methods to detect evidence. Such evidence includes blood, saliva, semen, and other body fluids; as well as hair, flesh, bone fragments, teeth, human skin damage such as bruises, bite marks or cuts; shoe prints, fingerprints, footprints, tire prints, gunpowder residue, bullets, explosives, chemical and biological agents, paint, grease or oil, glass fragments, fibers and various trace evidence, including the alteration of documents.

The detection of evidence has historically been a combined process of art and science. One conventional method of obtaining, for example, fingerprint evidence is the careful lifting of fingerprints by applying a fine dust to the surface of a fresh print and then transferring the dust pattern onto a second surface. Fingerprint dusting powders were initially selected for their color contrasting qualities. Extremely fine fluorescent dusting powders were also used to visualize minute etchings of a surface caused by the breakdown of amino acids contained in fingerprint oils. The fluorescent dusting powder adheres to the etchings and reveals the fingerprint pattern upon illumination by ultraviolet radiation. Other substances, such as blood, saliva or semen, are easily detected where visible stains exist. However, often such revealing evidence is concealed from ordinary inspection via cleansing agents or even the passage of time.

In more recent years, ultraviolet light has been used by forensic specialists to aid in the viewing of otherwise invisible evidence. Ultraviolet ("UV") radiation is light that is just beyond the visible spectrum. Whereas visible light has a wavelength ranging from about 400 nm to about 750 nm, UV radiation has a shorter wavelength and ranges from about 10 nm to about 400 nm. Although the unaided human eye cannot discern UV radiation, its presence can be shown by use of either UV-sensitive media or the resultant fluorescence of a UV-sensitive material. When fingerprints are dusted with fluorescent dusting powders, applied UV radiation will result in the fluorescing of the dusting powder, effectively making the fingerprints visible to the unaided eye. Other organic substances, such as saliva or semen, naturally fluoresce, and are thus also visible upon exposure to UV radiation.

Conventional UV fluorescence detection methods involve using a so called "black light" in the form of a continuous or non-flash flood-type UV source to continuously generate UV radiation near the evidence, and then using a camera with a filtered lens to capture the resultant fluorescent image onto film. Because the evidence will fluoresce at a relatively low intensity, light sensitive film and a relatively slow shutter speed are required. Additionally, the camera must also be held very close to the evidence. The effect, then, is a relatively narrow field scan that must be repeated many times to effectively detect evidence over a large area.

Variations on conventional UV fluorescence detection methods include the use of chemical reagents or vapors to deposit fluorescence-emitting particles onto fingerprint etchings where regular dusting methods are not appropriate. A laser, instead of a black light, may also be used to excite the fluorescence-emitting material. However, laser excitation is, by its very nature, limited to use over a small overall area. Additionally, the portability and use of a laser in small areas may be limited due to the large power supply required for operation of the laser.

A more recent UV detection method utilizes UV reflectance instead of fluorescence. Although the reflected UV detection method may not result in the clean images produced by UV fluorescence, high-intensity short-wave UV reflectance can reveal otherwise undetectable or difficult to detect evidence on non-porous surfaces that limit the use of fluorescent dusts or dyes.

Analysis of evidence detected through UV fluorescence or reflectance generally includes the development and close examination of photographs taken of the UV-detected evidence to determine the exact locations of the evidence. Dimensions of the detected evidence and overall shape are often obtained by hand measurement or even sketched reproduction. The substance of the evidence is determined by DNA testing as well as by other tests for specific reagents.

BRIEF SUMMARY OF THE INVENTION

The present invention is directed to a method and system for detecting and analyzing forensic evidence. In one embodiment of the present invention, a method for detecting and analyzing forensic evidence is provided. A background fluorescence image of a suspected-evidence area is digitally captured. The suspected-evidence area is exposed to a pulse of ultraviolet radiation and an evidence-exposing fluorescence image of the suspected-evidence area is digitally captured. The background fluorescence image and the evidence-exposing fluorescence image are processed to create a composite evidence image. The composite evidence image is analyzed to determine one or more fluorescing wavelengths emanating from a corresponding one or more evidence regions within the suspected-evidence area. The composite evidence image and analysis results are displayed for evaluation.

In another embodiment of the present invention, a forensic evidence detection and analysis system is provided. The system includes a digital camera and an ultraviolet light source configured to pulse high-intensity ultraviolet radiation. A computer and display are also provided for processing and controlling the capturing of the images according to a computer program installed on the computer. The computer program is configured to process and analyze fluorescent images of an area illuminated by the ultraviolet light source and as captured by the digital camera.

BRIEF DESCRIPTION OF THE SEVERAL VIEWS OF THE DRAWINGS

Embodiments of the present invention will now be described, by way of example only, with reference to the following drawings in which.

DETAILED DESCRIPTION OF THE INVENTION

The present invention is described by reference to the associated drawing figures. Identical labels and numbers in multiple drawing figures are meant to represent the same elements in each drawing figure.

Figure 1:
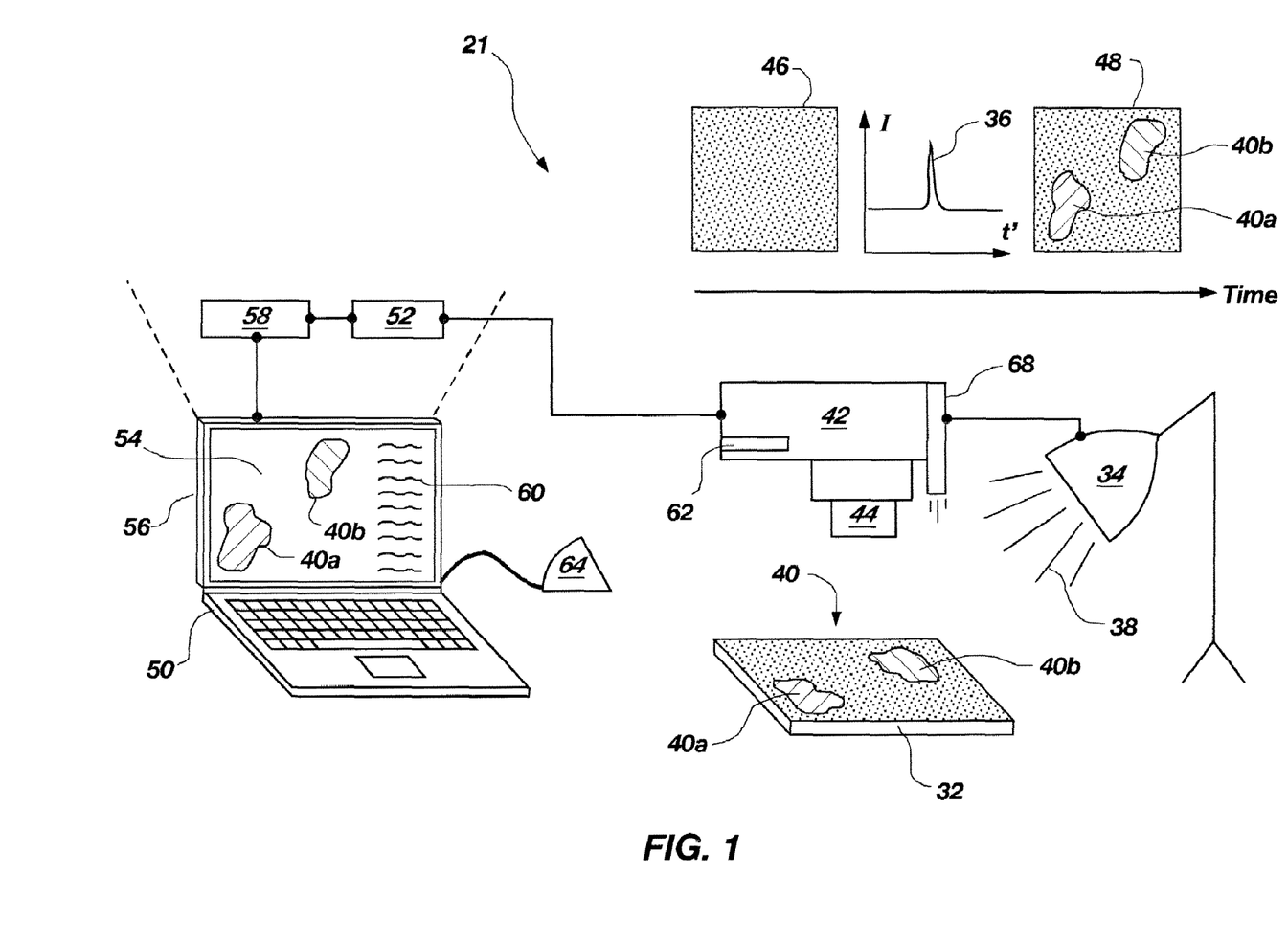
FIG. 1 is a simplified diagram of a combined forensic evidence detection and analysis system, in accordance with an embodiment of the present invention.
Figure 2:
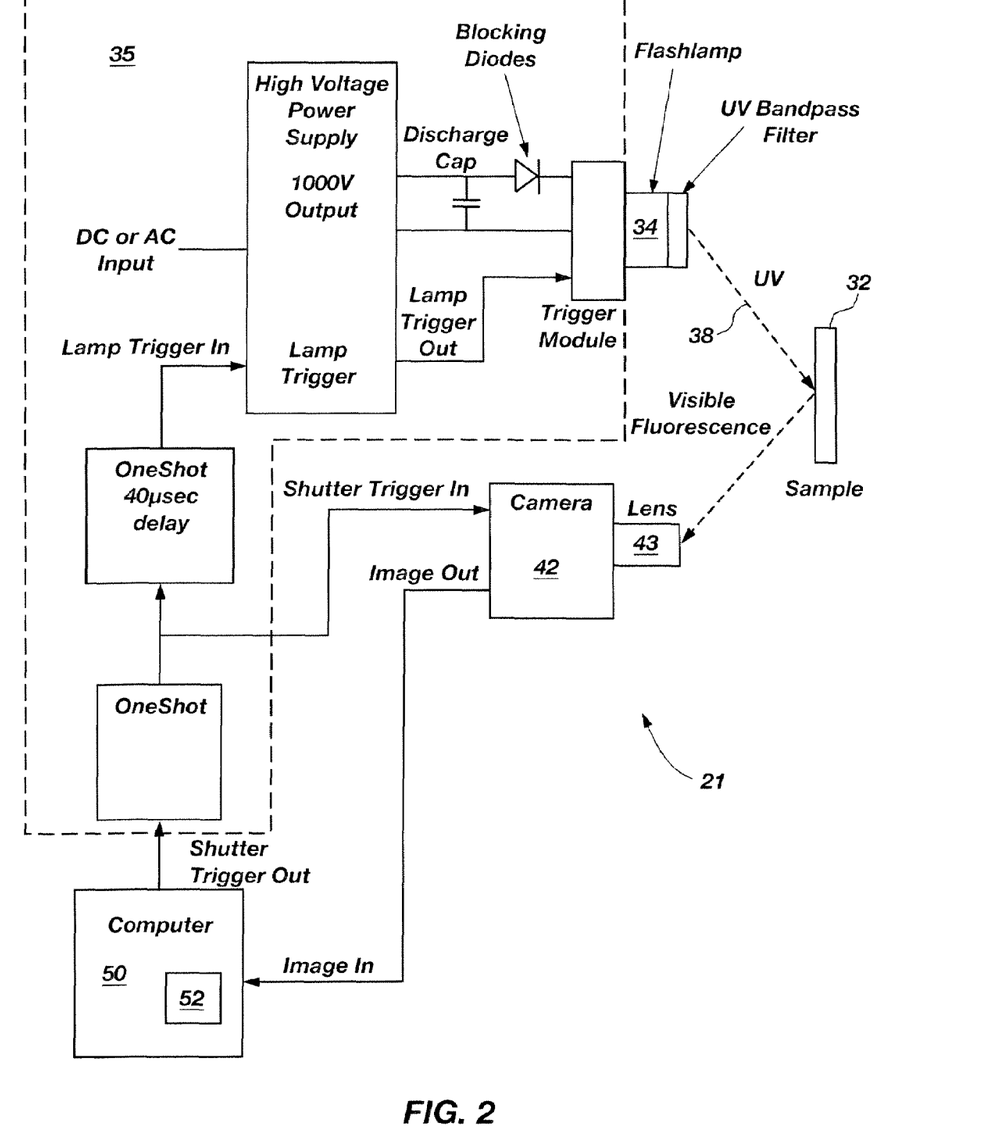
FIG. 2 is a schematic diagram of a combined forensic evidence detection and analysis system in accordance with an embodiment of the present invention.

FIG. 1 is a simplified diagram and FIG. 2 is a schematic diagram of a combined forensic evidence detection and analysis system 21, in accordance with an embodiment of the present invention. In the current embodiment, a digital camera 42, such as an intensified charge coupled device ("CCD") camera or digital camcorder equipped with a UV filter 44, is used to take an image of a suspected area of evidence 32. An initial background image 46 is taken of the suspected area of evidence 32 to indicate background levels of ambient UV reflected and fluorescent light. An evidence-exposing fluorescence image including the background image 46 or evidence-plus-background image 48 is taken immediately after the suspected area of evidence 32 is exposed to a flash UV light source 34. The flash UV light source 34 generates a high-intensity pulse 36 of UV radiation 38. The high-intensity pulse 36 of UV radiation 38 excites evidence 40 (evidence types 40a, 40b) such that evidence 40 fluoresces.

The flash UV system uses UV light to inspect areas that may be contaminated. The system operates by pulsing the light through a triggering device that also activates the shutter of a CCD camera, which takes a digital picture of the resultant fluorescence. In addition to the CCD camera, supporting software for the camera allows changes to the gain settings and sensitivity to the wavelengths of interest. The various embodiments of the present invention allow an investigator to photograph areas of interest without normal photographic film, which may or may not show the image that the investigator sees. The camera, through the use of notch filters, and software allow the investigator to use various wavelengths.

UV flash fluorescence is luminescence due to absorption of UV radiation by outer shell electrons followed by immediate re-radiation (fluorescence) in the form of visible light that ceases almost as soon as the incident UV radiation stops (atoms return to the ground state). The pulsed light gives a greater equivalent of power than the continuous UV source found in hand held backlights (approximately 50 kW compared to 100 W from a continuous source).

The initial background image 46 and the evidence-plus-background image 48 are transferred to a computer 50. An image processing package 52 subtracts the initial background image 46 from the evidence-plus-background image 48, resulting in a composite evidence or an evidence-only image 54. The evidence-only image 54 is displayed on the computer display 56. The evidence-only image 54 is also analyzed by an image analysis package 58, resulting in analysis data 60.

The components of the combined forensic evidence detection and analysis system 21, i.e., the flash UV light source 34, the digital camera 42 and the computer 50, are interconnected such that the digital camera 42, including lens 43, will only take the evidence-plus-background image 48 immediately after a pulse of the flash UV light source 34. This timing control 35 may be implemented via a direct connection between the flash UV light source 34 and the digital camera 42, or, alternatively, it may be implemented via software control, meaning that both the flash UV light source 34 and the digital camera 42 are connected to the computer 50. Additionally, transfer of image data between the digital camera 42 and computer 50 may be accomplished through a variety of methods. Image data may be stored by the digital camera 42 onto a storage medium 62, which storage medium 62 may be transferred to an appropriate media-reading device 64 connected to the computer 50. Image data may also be transferred directly from the digital camera 42 to the computer 50 via a hard-wired or wireless connection. By way of example and not limitation, an exemplary suitable camera may include a "Retiga 1300i" available from Q Imaging of Burnaby, B.C., Canada.

Other control systems include a range-finding system 68, preferably utilizing a range-finding laser, connected to either the digital camera 42 or the flash UV light source 34. The range-finding system 68 will only allow the forensic evidence detection and analysis system 21 to function when the digital camera 42 and the flash UV light source 34 are within an appropriate range of the suspected area of evidence 32.

The flash UV light source 34 is implemented by use of a lamp that emits a high-intensity pulse 36 of radiation in the UV, visible and infra-red ("IR") ranges. Specifically, the flash UV light source 34 emits radiation in the ranges of 140 nm to 1100 nm, and may emit either a wide-band pulse or a tunable narrow-band pulse at a specific wavelength. The high-intensity pulse 36 is of sufficient intensity to adequately illuminate a suspected area of evidence 32 that is many square feet in area, from a distance of several feet. Additionally, the high-intensity pulse 36 is of sufficient intensity to cause to fluoresce any fluorescent evidence 40 within the illuminated area of the suspected area evidence 32. By way of example, the suspected area of evidence 32 may be on the order of multiple square inches to multiple square feet, depending on the range and resolution of the digital camera 42. In one example, the focal length of the digital camera 42 is on the order of tens of inches. By way of example and not limitation, exemplary suitable UV light sources include a "Perkin-Elmer FX-249U" (Xenon lamp, 4 Joules/flash, 60 W power) or a "Perkin-Elmer FX-4400" (Xenon lamp w/parabolic reflector, 1 Joule/flash, 60 W power) both available from PerkinElmer Optoelectronics of Fremont, Calif.

By way of example and not limitation, most of the materials of forensic interest fluoresce at approximately 300 nm. The system through the changing of sources and the use of filters is capable of working with multiple wavelengths, and is not limited to any one wavelength. The present invention contemplates the use of multiple wavelength (300 nm, 350 nm, and 385 nm) sources, and firing, for example, them in sequence, with spectra for each excitation being collected. The composite spectrum could then be stored for each material in a library within the system. Through software signal processing of the spectra contamination type, the specific contamination type could be identified.

Specifically, the forensic evidence detection and analysis system 21 uses UV light to inspect the suspected area of evidence 32 that may be contaminated. According to the forensic evidence detection and analysis system 21, the flash UV light source 34 is not continuously activated. The light is pulsed through timing control 35 that also activates the shutter of the digital camera 42, which takes a digital image of the resultant fluorescence. In addition to the digital camera 42, the supporting software for the digital camera 42 allows changes to the gain settings and sensitivity to the wavelengths of interest. In the present embodiment, the digital camera 42 relieves for example, the forensic investigator from the need to photograph areas of interest with conventional light-sensitive photographic film, which may or may not show the image that the investigator perceives. The digital camera 42, through the use of filters 44 (e.g., one or more notch filters), and software allow, for example, the investigator to use a wavelength of choice; thus the technique is not limited, as are most black light systems, to any one fixed wavelength (e.g., 365 nm). By way of example and not limitation, exemplary suitable filters include: "Hoya U-340," UV Bandpass filter, 1-inch dia, center 340 nm, half transmittance width 85 nm, available from Hoya Corp. of Tokyo, Japan; "Andover UG-11", UV Bandpass filter, 1-inch dia, center 330 nm, half transmittance width 85 nm, available from Andover Corp. of Salem, N.H.; "Schott BG-38", Low wavelength bandpass, 1-inch dia, center 480 nm, half transmittance width 380 nm, available from Schott, Inc. of Elmsford, N.Y.

In fact, wavelengths in the present system may be selected based upon the anticipated substances of interest. For example, most substances of forensic interest (e.g., blood, saliva, semen, etc.) fluoresce at a wavelength of approximately 300nm. According to the system of the present embodiment, multiple wavelengths of UV radiation 38 may be utilized in conjunction with corresponding filters 44 to enhance fluorescence of specific substances of particular interest. Furthermore, multiple wavelengths (e.g., 300 nm, 350 nm, and 385 nm) may be consecutively sequenced with the corresponding spectra collected from each excitation. Further analysis may be performed beyond the initial location of the substances. For example, the composite spectrum of each substance may be stored in a reference library within the system. Through, for example, signal processing of the spectra resulting from the evidence under analysis, a specific type of substance may be correlated with reference to the reference spectra of the reference library.

Generally, UV fluorescence, according to the various embodiments of the present invention using the forensic evidence detection and analysis system 21, utilize luminescence due to absorption of UV radiation by outer shell electrons followed by immediate re-radiation (fluorescence) in the form of visible light that ceases almost as soon as the incident UV radiation stops (i.e., atoms return to the ground state). Employing the flash UV light source 34 provides a greater equivalent of power than is generally available through a continuous UV source (i.e., approximately 50 kW from a flash UV system compared to 100 W from a nonflash or continuous source).

Figure 3:
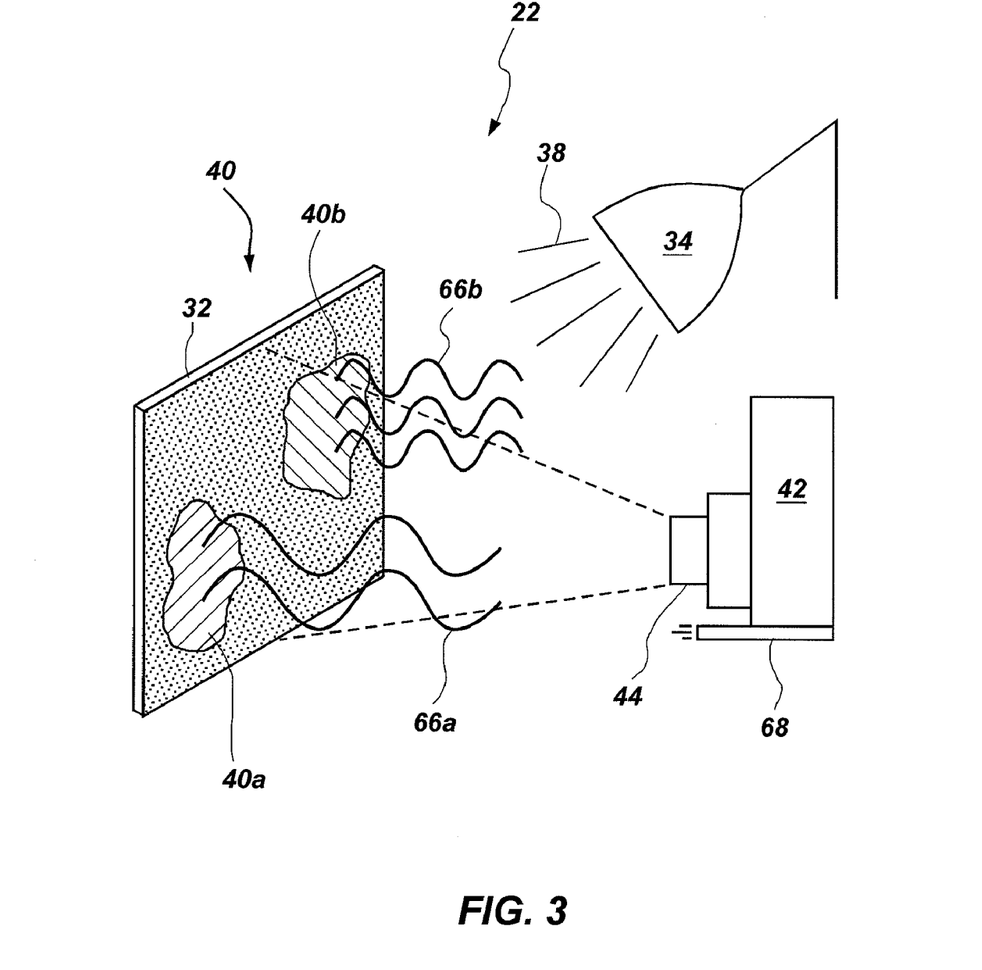
FIG. 3 shows a forensic evidence detection system, in accordance with an embodiment of the present invention.

FIG. 3 shows a forensic evidence detection system 22, in accordance with an embodiment of the present invention, wherein the evidence 40 includes multiple evidence types 40a and 40b. Evidence type 40a is excited at a specific wavelength contained in the spectrum of UV radiation 38 emitted by the flash UV light source 34. Evidence type 40a will subsequently fluoresce at a different fluorescing wavelength 66a. Evidence type 40b may similarly be excited at a specific wavelength contained in the spectrum of UV radiation 38 resulting in fluorescence at yet another fluorescing wavelength 66b. Saliva, semen, sweat, etc., each fluoresce at a distinguishing wavelength, thus allowing the image analysis package 58 (FIG. 1) to both distinguish and identify evidence types 40a and 40b.

Fingerprints, for example, will fluoresce if exposed to a sufficiently intense pulse of UV radiation without the use of dusting powders due to the energy of the pulsed UV source. Since more energy is available from the pulsed UV source than from conventional, continuous or non-flash sources, more of the UV radiation is absorbed which causes the fingerprints to fluoresce. Furthermore, the flash UV system is unlike a black light system because the pulsed system, due to the higher UV energy, is capable of being used in normal ambient lighting conditions. In contrast, a black light system must be used in a room with an extremely low ambient light level.

Blood, on the other hand, does not naturally fluoresce, but instead absorbs UV radiation. An area of absorbed UV radiation is still detectable in the evidence-plus-background image 48 as an area absent of any reflected or fluoresced UV radiation. Detection of the multiple fluorescing wavelengths 66a and 66b requires a UV filter 44 to be attached to the digital camera 42. The UV filter 44 may include multiple filters for specific fluorescing wavelengths 66a and 66b or a single tunable filter. The UV filter 44 will collectively pass UV wavelengths in the range of 330 nm to 450 nm. Additionally, the range-finding system 68 is shown connected to the digital camera 42, assisting proper orientation and positioning of the digital camera 42 and flash UV light source 34 to within an acceptable range of the suspected area of evidence 32.

Figure 4:
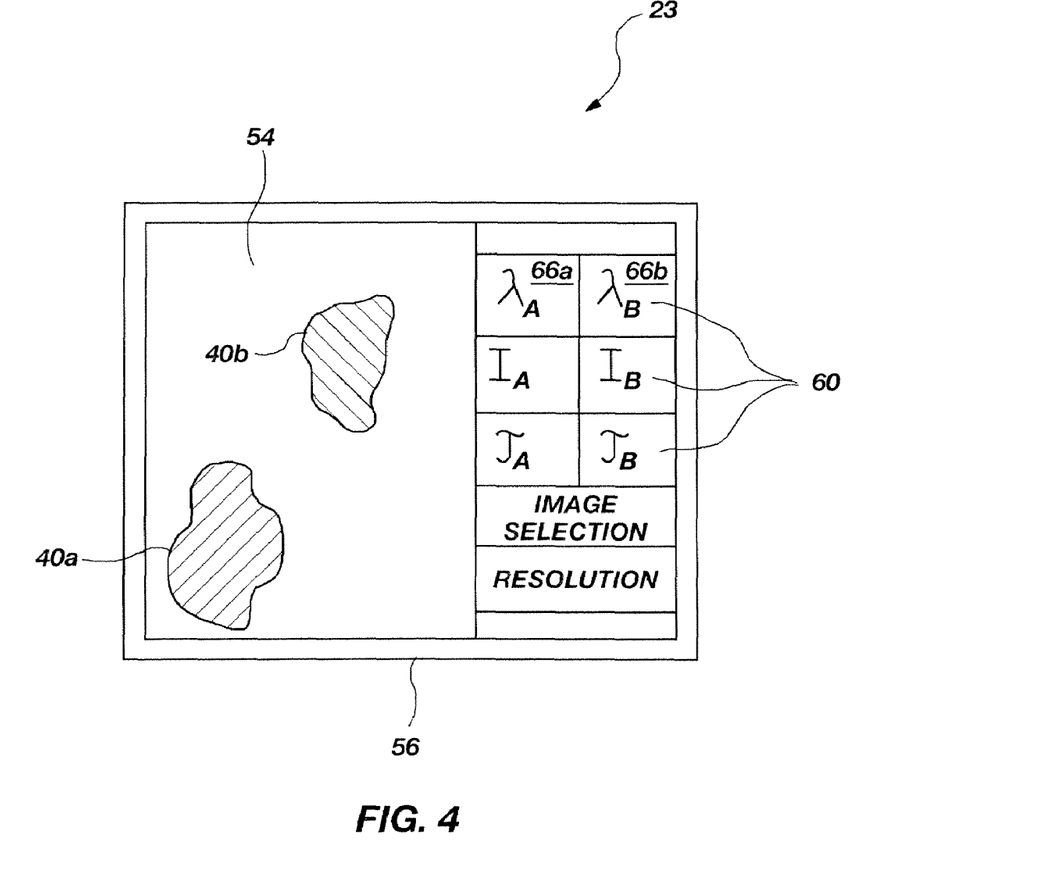
FIG. 4 is an exemplary display device, in accordance with an embodiment of the present invention.

FIG. 4 illustrates an exemplary display 23, in accordance with an embodiment of the present invention. Computer display 56 shows the evidence-only image 54, although other images, such as the initial background image 46 (FIG. 1) and the evidence-plus-background image 48 (FIG. 1) may also be viewed. The sampled resolution of the viewed images may be selected. Additionally, analysis data 60 collected from the image analysis package 58 (FIG. 1) may also be displayed. In FIG. 4, two evidence types 40a and 40b are shown. For each evidence type 40a, 40b, a fluorescing wavelength 66a and 66b and fluorescence intensity may be indicated. The size and location of the evidence types 40a, 40b are also indicated. Additionally, in another embodiment of the present invention, multiple evidence-plus-background images 48 (FIG. 1) may be rapidly taken so as to allow calculation by the image analysis package 58 (FIG. 1) of a fluorescence time constant for each evidence type 40a, 40b, indicating the attenuation rate of each fluorescing wavelength 66a, 66b.

The foregoing detailed description of the present invention is provided for purposes of illustration and is not intended to be exhaustive or to limit the invention to the precise embodiment disclosed. Accordingly, the scope of the present invention is defined by the following claims.

What is claimed is:

1. A method for detecting and analyzing forensic evidence, comprising:
   digitally capturing a background fluorescence image of a suspected-evidence area;
   exposing the suspected-evidence area to a pulse of ultraviolet radiation;
   digitally capturing an evidence-exposing fluorescence image of the suspected-evidence area;
   Using a processor (or computer) to perform the steps of:
   processing the background fluorescence image and the evidence-exposing fluorescence image to create a composite evidence image;
   analyzing the composite evidence image to determine one or more fluorescing wavelengths emanating from a corresponding one or more evidence regions within the suspected-evidence area; and
   displaying the composite evidence image and analysis results.

2. The method of claim 1, wherein exposing the suspected-evidence area comprises using a light source that emits radiation in a range of 140 to 1100 nanometers.

3. The method of claim 1, wherein exposing the suspected-evidence area comprises using a tunable light source that selectively emits radiation in a range of 140 to 1100 nanometers.

4. The method of claim 1, wherein exposing the suspected-evidence area comprises using sufficiently intense UV radiation to excite fluorescence of fluorescent evidence within the suspected-evidence area.

5. The method of claim 1, wherein exposing the suspected-evidence area comprises exposing an area comprising at least a plurality of square feet from a distance of several feet.

6. The method of claim 1, wherein exposing the suspected-evidence area comprises using a range-finding system to place a high-intensity pulse of ultraviolet radiation within a sufficient range of the suspected-evidence area.

7. The method of claim 1, wherein digitally capturing one of the background fluorescence image and the evidence-exposing fluorescence image comprises using a digital camera.

8. The method of claim 7, further comprising transferring the background fluorescence and evidence-exposing fluorescence images from the digital camera to a computer for processing, analyzing and displaying.

9. The method of claim 8, wherein transferring the background fluorescence and evidence-exposing fluorescence images comprises storing the background fluorescence and evidence-exposing fluorescence images from the digital camera onto a storage medium and reading the background fluorescence and evidence-exposing fluorescence images into the computer via a media-reading device.

10. The method of claim 1, wherein digitally capturing one of the background fluorescence image and the evidence-exposing fluorescence image comprises using an ultraviolet filter that passes radiation in a range of 330 to 450 nanometers.

11. The method of claim 1, wherein digitally capturing one of the background fluorescence image and the evidence-exposing fluorescence image comprises using a tunable ultraviolet filter that selectively passes radiation in a range of 330 to 450 nanometers.

12. The method of claim 1, wherein processing the background fluorescence and evidence-exposing fluorescence images comprises creating a composite evidence image by subtracting the background fluorescence image from the evidence-exposing fluorescence image.

13. The method of claim 1, wherein analyzing the composite evidence image comprises determining a size and location for each of the corresponding one or more evidence regions.

14. The method of claim 1, wherein analyzing the composite evidence image comprises determining a fluorescence intensity for each of the corresponding one or more of evidence regions.

15. The method of claim 1, wherein displaying the composite evidence image and the analysis results comprises displaying immediately after capturing the evidence-exposing fluorescence image.

16. The method of claim 1, wherein analyzing the composite evidence image comprises determining a one or more of ultraviolet-absorbing regions.

17. The method of claim 1, wherein:
digitally capturing an evidence-exposing fluorescence image comprises digitally capturing one or more evidence-exposing fluorescence images within a sufficiently short period of time immediately after the exposure of the suspected-evidence area;
processing the background fluorescence and evidence-exposing fluorescence images comprises processing the background fluorescence image and the one or more of evidence-exposing fluorescence images to create a one or more of composite evidence images;
analyzing the composite evidence image comprises analyzing the one or more of composite evidence images to determine a one or more of fluorescing wavelengths emanating from a corresponding one or more of evidence regions within the suspected-evidence area; and
displaying the composite evidence image comprises displaying the one or more of composite evidence images and analysis results.

18. The method of claim 17, wherein analyzing the one or more of composite evidence images comprises determining a plurality of time constants indicating an attenuation time for each of the one or more of fluorescing wavelengths emanating from each of the corresponding one or more of evidence regions within the suspected-evidence area.

19. A forensic evidence detection and analysis system, comprising:
a digital camera configured for digitally capturing a background fluorescence image of a suspected-evidence area;
an ultraviolet light source configured to pulse high-intensity ultraviolet radiation on the suspected-evidence area, the digital camera further configured for digitally capturing an evidence-exposing fluorescence image of the suspected-evidence area;
a computer and display configured for displaying composite evidence image and analysis results; and
a computer program installed on the computer, configured for processing the background fluorescence image and the evidence-exposing fluorescence image to create the composite evidence image and for analyzing the composite evidence image to determine one or more fluorescing wavelengths emanating from a corresponding one or more evidence regions within the suspected-evidence area.

20. The forensic evidence detection and analysis system of claim 19, wherein the digital camera further includes an ultraviolet filter or a set of ultraviolet filters adapted to pass radiation in a range of 330 to 450 nanometers.

21. The forensic evidence detection and analysis system of claim 19, wherein the digital camera includes a tunable ultraviolet filter adapted to selectively pass radiation in a range of 330 to 450 nanometers.

22. The forensic evidence detection and analysis system of claim 19, further comprising a range-finding system to determine a distance between the digital camera and a suspected-evidence area.

23. The forensic evidence detection and analysis system of claim 19, wherein the ultraviolet light source is configured to pulse high-intensity radiation in a range of 140 to 1100 nanometers.

24. The forensic evidence detection and analysis system of claim 19, wherein the ultraviolet light source is tunable to selectively pulse high-intensity radiation in a range of 140 to 1100 nanometers.

25. The forensic evidence detection and analysis system of claim 19, wherein the ultraviolet light source is configured to expose an area of many square feet from a distance of several feet.

26. The forensic evidence detection and analysis system of claim 19, wherein the ultraviolet light source is configured to emit ultraviolet radiation to excite fluorescence of one or more fluorescent evidences within an area illuminated thereby.

27. The forensic evidence detection and analysis system of claim 19, wherein the computer program is adapted to create a composite evidence image created by subtracting the background fluorescence image from the evidence-exposing fluorescence image.

28. The forensic evidence detection and analysis system of claim 19, wherein the computer program is adapted to determine a one or more of fluorescing wavelengths from a corresponding one or more of evidence regions in an image.

29. The forensic evidence detection and analysis system of claim 19, wherein the computer program is adapted to determine a one or more of fluorescence intensities for a corresponding one or more of evidence regions in an image.

30. The forensic evidence detection and analysis system of claim 19, wherein the computer program is adapted to determine a one or more time constant indicating an attenuation time for each of a corresponding one or more of fluorescing wavelengths emanating from each of a corresponding one or more evidence regions.

31. The forensic evidence detection and analysis system of claim 19, further comprising means to communicate between the digital camera, the ultraviolet light source and the computer and display.

\* \* \* \* \*